(12) United States Patent
Schader et al.

(10) Patent No.: US 12,268,853 B2
(45) Date of Patent: Apr. 8, 2025

(54) DRUG DELIVERY DEVICE WITH DRIVE SUB-ASSEMBLY

(71) Applicant: Sanofi, Paris (FR)

(72) Inventors: Marc Schader, Frankfurt am Main (DE); Michael Mayer, Frankfurt am Main (DE); Jim Bradford, Cambridgeshire (GB); William Timmis, Cambridgeshire (GB); Thomas Mark Kemp, Cambridgeshire (GB); Hugo Revellat, Cambridgeshire (GB)

(73) Assignee: Sanofi, Paris (FR)

( * ) Notice: Subject to any disclaimer, the term of this patent is extended or adjusted under 35 U.S.C. 154(b) by 1231 days.

(21) Appl. No.: 16/960,249

(22) PCT Filed: Nov. 1, 2018

(86) PCT No.: PCT/EP2018/079938
§ 371 (c)(1),
(2) Date: Jul. 6, 2020

(87) PCT Pub. No.: WO2019/086576
PCT Pub. Date: May 9, 2019

(65) Prior Publication Data
US 2021/0069420 A1 Mar. 11, 2021

(30) Foreign Application Priority Data
Nov. 3, 2017 (EP) ..................................... 17306524

(51) Int. Cl.
*A61M 5/315* (2006.01)
*A61M 5/20* (2006.01)
(Continued)

(52) U.S. Cl.
CPC ........ *A61M 5/3157* (2013.01); *A61M 5/2033* (2013.01); *A61M 5/3146* (2013.01);
(Continued)

(58) Field of Classification Search
CPC .............. A61M 5/3157; A61M 5/2033; A61M 5/3146; A61M 5/31511; A61M 5/31583;
(Continued)

(56) References Cited

U.S. PATENT DOCUMENTS

2013/0324925 A1* 12/2013 Brereton ................. A61M 5/46
604/110

FOREIGN PATENT DOCUMENTS

EP 2923714 9/2015
EP 2923714 A1 * 9/2015 .......... A61M 5/2033
(Continued)

OTHER PUBLICATIONS

PCT International Preliminary Report on Patentability in International Appln. No. PCT/EP2018/079938, dated May 5, 2020, 6 pages.
(Continued)

*Primary Examiner* — Nathan R Price
*Assistant Examiner* — Haden Matthew Ritchie
(74) *Attorney, Agent, or Firm* — Fish & Richardson P.C.

(57) ABSTRACT

The present disclosure relates to a drive subassembly for a drug delivery device, the drive subassembly comprising a housing and a plunger, wherein the plunger is adapted to be rotated between a locked position, in which the plunger is prevented from advancing, and a released position, in which the plunger is advancable, wherein at least one restraining component is provided to restrain rotation of the plunger from the locked position towards the released position.

21 Claims, 11 Drawing Sheets

(51) Int. Cl.
  *A61M 5/31* (2006.01)
  *A61M 5/32* (2006.01)
(52) U.S. Cl.
  CPC .... *A61M 5/31511* (2013.01); *A61M 5/31583* (2013.01); *A61M 5/3202* (2013.01); *A61M 2205/581* (2013.01); *A61M 2205/582* (2013.01)
(58) Field of Classification Search
  CPC ............ A61M 5/3202; A61M 5/31571; A61M 2205/581; A61M 2205/582; A61M 2005/208
  See application file for complete search history.

(56) References Cited

FOREIGN PATENT DOCUMENTS

| | | | |
|---|---|---|---|
| JP | 2017-508546 | 3/2017 | |
| WO | WO 2011/123024 | 10/2011 | |
| WO | WO-2011123024 A1 * | 10/2011 | ............ A61M 5/145 |
| WO | WO 2015/144870 | 10/2015 | |

OTHER PUBLICATIONS

PCT International Search Report and Written Opinion in International Appln. No. PCT/EP2018/079938, dated Dec. 19, 2018, 9 pages.

* cited by examiner

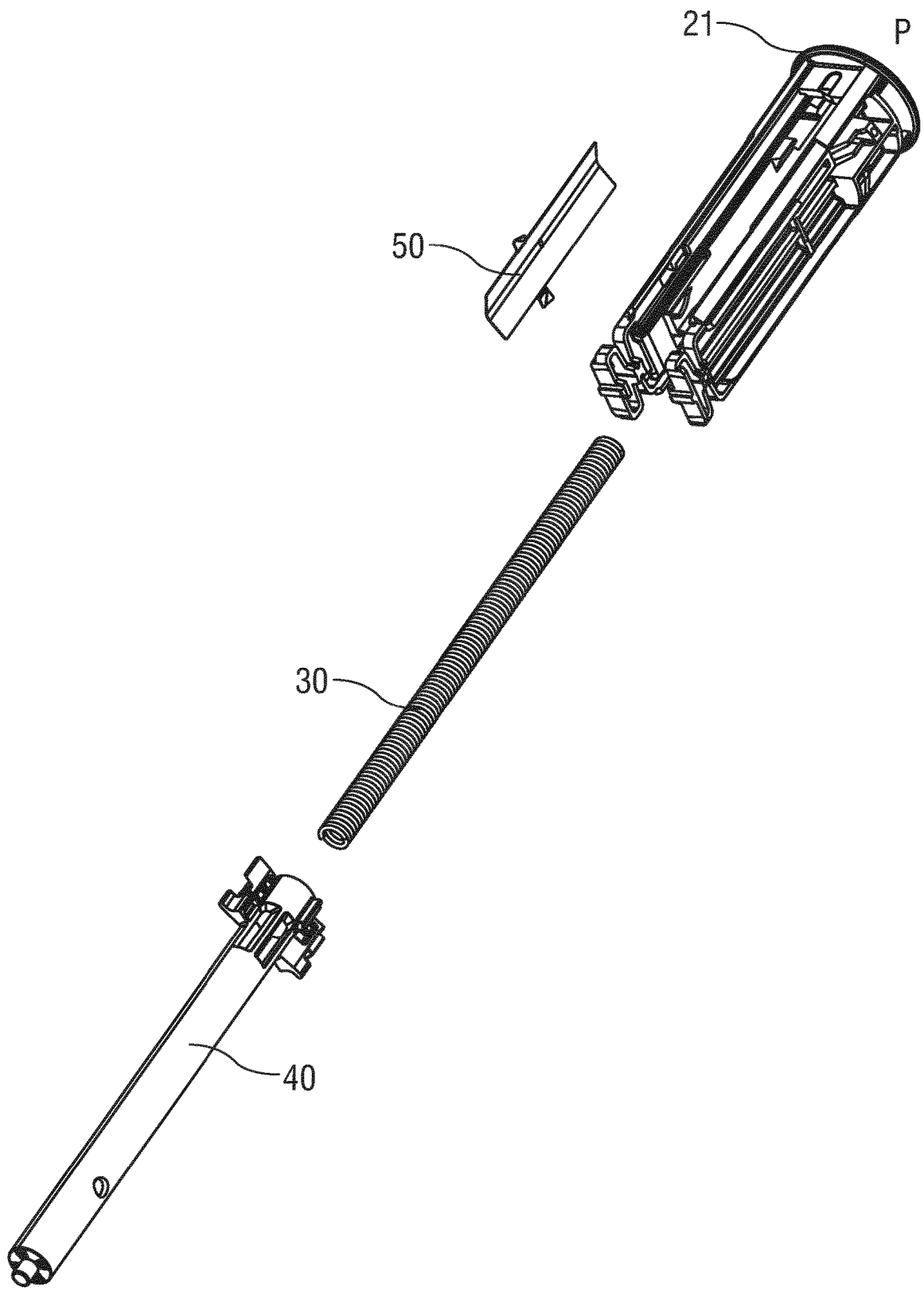

DRUG DELIVERY DEVICE WITH DRIVE SUB-ASSEMBLY

CROSS-REFERENCE TO RELATED APPLICATIONS

The present application is the national stage entry of International Patent Application No. PCT/EP2018/079938, filed on Nov. 1, 2018, and claims priority to Application No. EP 17306524.4, filed on Nov. 3, 2017, the disclosures of which are incorporated herein by reference.

TECHNICAL FIELD

The disclosure generally relates to a drug delivery device having a drive subassembly.

BACKGROUND

Drug delivery devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

Plunger release mechanisms are applied to control motion of a plunger in a drug delivery device in a manner keeping the plunger in a defined position until a condition is met suddenly allowing the plunger to move within the drug delivery device thus delivering a dose of a drug from a syringe.

The drug delivery device may be divided in two subassemblies, a control subassembly and a drive subassembly. This allows for improving flexibility as to the time and location of manufacture of the subassemblies and final assembly with the syringe.

There remains a need for an improved drug delivery device.

SUMMARY

An object of the present disclosure is to provide an improved drug delivery device.

The object is achieved by a drug delivery device according to claim 1.

Exemplary embodiments are provided in the dependent claims.

According to the present disclosure, a drug delivery device comprises:
- a drive subassembly for a drug delivery device comprises a housing or part thereof, in particular a proximal region, and a plunger, wherein the plunger is adapted to be rotated between a locked position, in which the plunger is prevented from advancing, and a released position, in which the plunger is advancable, wherein at least one restraining component is provided to restrain rotation of the plunger from the locked position towards the released position, and
- a control subassembly comprising a distal region of the housing adapted to receive a syringe and a sleeve coupled to the housing to permit movement of the sleeve relative to the housing to release the plunger.

The present disclosure may help prevent inadvertent release of the plunger when the drug delivery device or a part thereof, in particular the drive subassembly, is dropped, for example if the drive subassembly is dropped onto a distal tip of the plunger. By avoiding inadvertent plunge release during assembly, safety may be increased as the unrestrained plunger and a drive spring may travel at high speed when released. Furthermore, the present disclosure may help reduce the amount of scrap parts.

In an exemplary embodiment, the at least one restraining component comprises a deformable housing protrusion on the housing and a plunger boss or edge on the plunger adapted to abut the housing protrusion when the plunger is rotated from the locked position towards the released position and adapted to deform the housing protrusion upon further rotation of the plunger towards the released position.

In an exemplary embodiment, the housing protrusion protrudes radially inwards.

In an exemplary embodiment, the plunger boss comprises a radial plunger protrusion adapted to abut the housing protrusion.

In an exemplary embodiment, the plunger protrusion or the plunger boss comprises a chamfer adapted to engage the housing protrusion when the plunger is rotated from the released position towards the locked position.

In an exemplary embodiment, the plunger boss is resiliently or plastically deformable.

In an exemplary embodiment, the housing protrusion protrudes in a distal direction.

In an exemplary embodiment, the edge is arranged on a recess within a proximal face of the plunger.

In an exemplary embodiment, the at least one restraining component comprises a transversal component and a plunger boss on the plunger adapted to abut the transversal component when in the locked position and being moved in a proximal direction so as to restrain proximal movement of the plunger.

In an exemplary embodiment, the transversal component is a housing beam comprising a fixed end coupled to the housing and a free end, the free end comprising a distal protrusion adapted to abut the plunger boss upon rotation of the plunger from the locked position towards the released position.

In an exemplary embodiment, the distal protrusion comprises a chamfer adapted to engage the plunger boss when the plunger is rotated from the released position towards the locked position.

In an exemplary embodiment, the housing beam is resiliently or plastically deformable.

In an exemplary embodiment, the transversal component comprises at least one rounded or chamfered edge to engage the plunger boss.

In an exemplary embodiment, the transversal component is axially positioned to allow an axial clearance between the plunger boss and the transversal component when the plunger is being moved out of the locked position.

In an exemplary embodiment, the at least one restraining component comprises a plunger boss on the plunger and an indent in the housing, the plunger boss having a proximal boss protruding in a proximal direction adapted to be received within the indent so as to restrain rotation of the plunger from the locked position towards the released position.

In an exemplary embodiment, the indent comprises a ramp adapted to guide the proximal boss into the indent and rotate the plunger towards the locked position.

In an exemplary embodiment, a ramp is provided on the housing adapted to engage the plunger during assembly of the plunger into the housing and to rotate the plunger towards the locked position upon movement of the plunger in the proximal direction relative to the housing.

In an exemplary embodiment, the drive subassembly further comprises a drive spring adapted to bias the plunger in the distal direction relative to the housing.

In an exemplary embodiment, the at least one restraining component is adapted to restrain rotation of the plunger from the locked position towards the released position during a priming step.

In an exemplary embodiment, the drug delivery device comprises a syringe containing a medicament.

In an exemplary embodiment, the sleeve comprises a sleeve rib having a longitudinal face interacting with a plunger boss, wherein preferably, as the sleeve is being moved from an extended position towards a retracted position, the plunger boss moves relative to the sleeve in the distal direction guided along the longitudinal face of the sleeve rib until the plunger boss has moved distally beyond the sleeve rib such that the plunger is no longer prevented from rotating in the first rotational direction, e.g. due to torque induced by the drive spring and a plunger boss engaging an angled surface on a profiled slot in the housing, e.g the proximal region thereof.

In an exemplary embodiment, proximal movement of the sleeve, e.g. by placing a distal end of sleeve against a patient's body, and moving housing in a distal direction may uncover the distal end of needle.

In an exemplary embodiment, when the drug delivery device is assembled, the distal region and the proximal region of the housing are fixed to each other so that relative movement between the distal region and the proximal region is prevented.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein:

FIG. 2 is a schematic perspective exploded view of a drive subassembly of a drug delivery device.

Corresponding parts are marked with the same reference symbols in all figures.

DETAILED DESCRIPTION

Figure 1A:
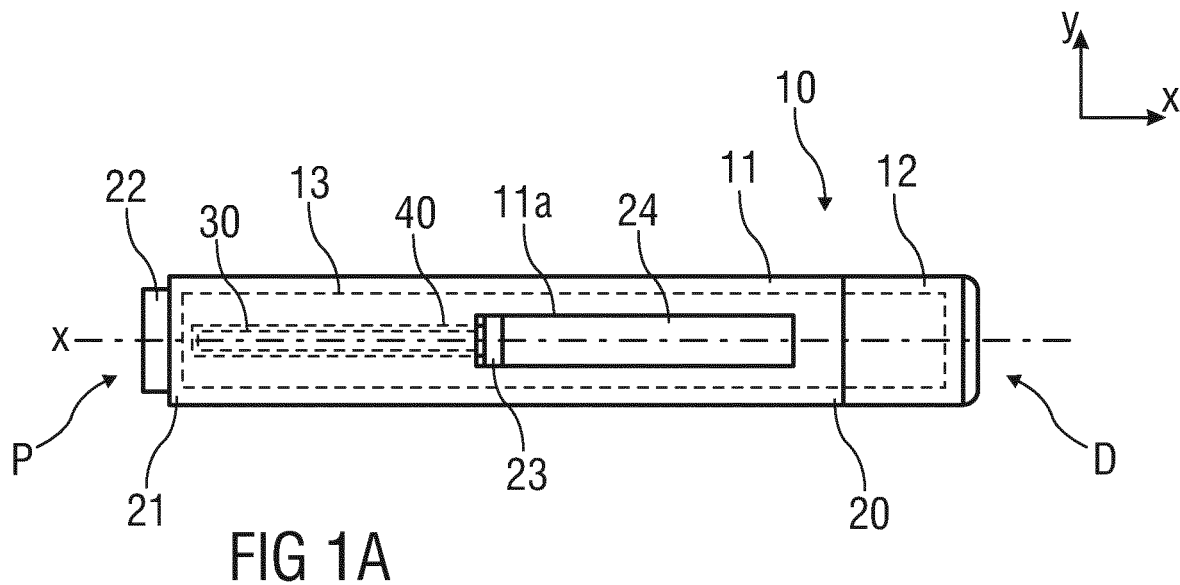
FIG. 1 is a schematic view of an exemplary embodiment of a drug delivery device.
Figure 1B:
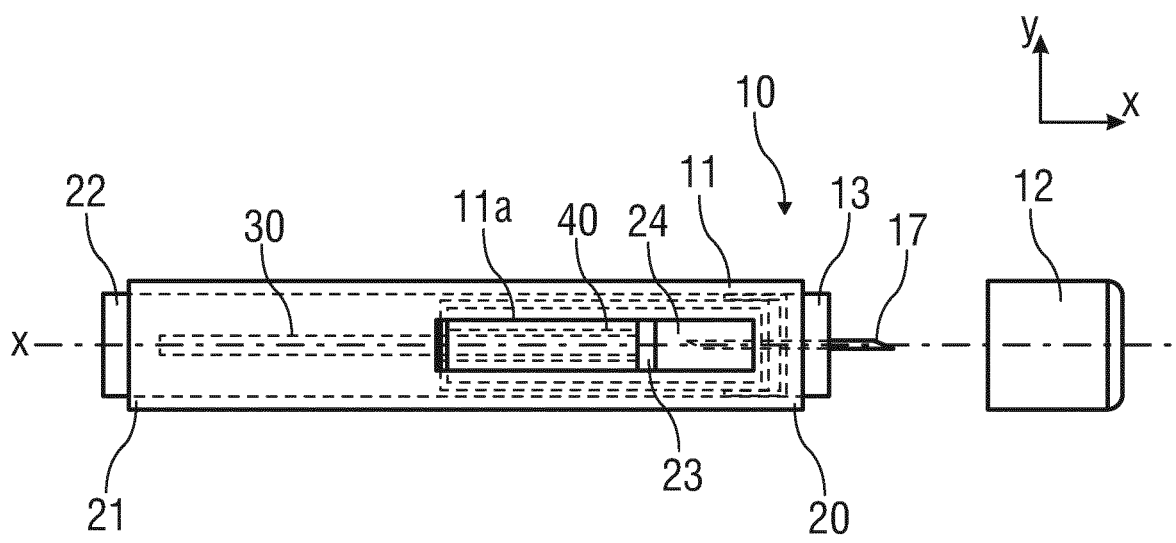

According to some embodiments of the present disclosure, an exemplary drug delivery device 10 is shown in FIGS. 1A and 1B.

Device 10, as described above, is configured to inject a drug or medicament into a patient's body.

Device 10 includes a housing 11 which typically contains a reservoir containing the medicament to be injected (e.g., a syringe 24 or a container) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal region 20 of housing 11.

Insertion of the needle 17 can occur via several mechanisms. For example, the needle 17 may be fixedly located relative to housing 11 and initially be located within an extended needle sleeve 13. Proximal movement of the sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to housing 11. Such insertion can be triggered by movement of sleeve 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a sleeve trigger mechanism, e.g. provided by pushing the needle sleeve 13 inside the housing when the drug delivery device is put onto an injection side.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, an energy source, e.g. a drive spring 30 is arranged in a plunger 40 and is under compression before device 10 is activated. A proximal end of the drive spring 30 can be fixed within proximal region 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing 11 may comprise a window 11a through which the syringe 24 can be monitored.

The drug delivery device 10 may be divided in two subassemblies, a control subassembly and a drive subassembly 10.1. This allows for improving flexibility as to the time and location of manufacture of the subassemblies and final assembly with the syringe 24.

FIG. 2 is a perspective exploded view of the drive subassembly 10.1. The drive subassembly 10.1 comprises components used to displace the medicament from the syringe 24. If the viscosity or volume of the medicament M in the syringe 24 is varied, only parts of the drive subassembly 10.1 may need to be changed. The drive subassembly 10.1 comprises the plunger 40, the drive spring 30 and the proximal region 21 of the housing 11. In an exemplary embodiment, the drive subassembly 10.1 may be assembled in a process which requires virtually only axial motion except for the plunger 40. In order to assemble the drive subassembly 10.1 the drive spring 30 is inserted into the plunger 40 and the plunger 40 is inserted in the proximal region 21 in the proximal direction P thereby compressing the drive spring 30. Once the plunger 40 reaches a compressed position it is rotated by an angle, e.g. approximately 30° to lock it to the proximal region 21. In an exemplary embodiment the proximal region 21 could have a cam surface which could induce this rotation prior to the plunger 40 reaching the compressed position.

Furthermore, a feedback element 50, e.g. a spring element may be provided to indicate an event, e.g. an end of dose, by providing an audible and/or tactile feedback.

Figure 3:
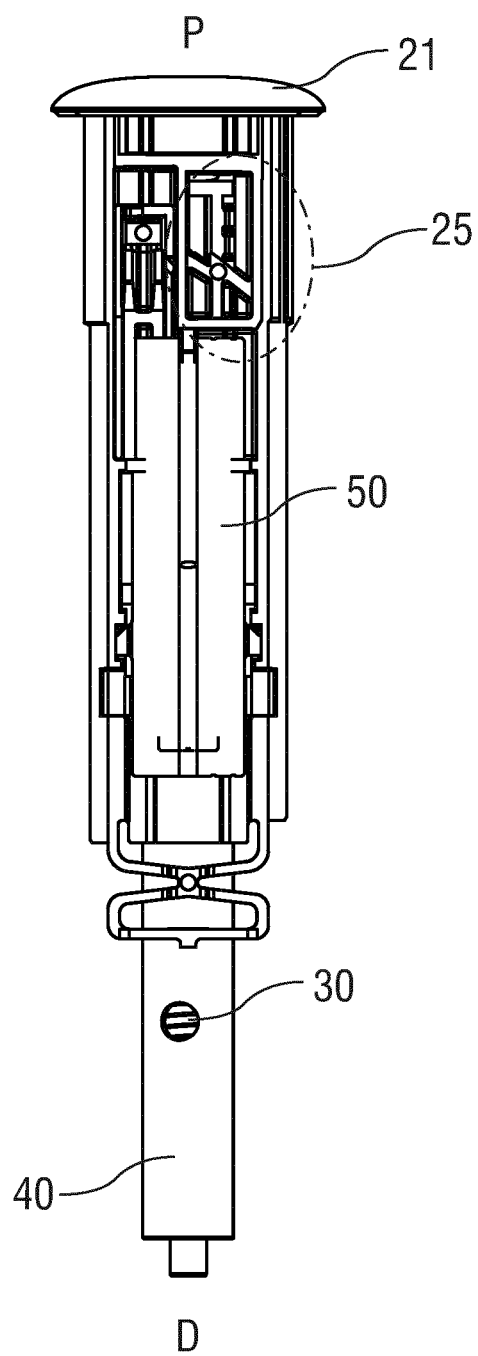
FIG. 3 is a schematic side view of the drive subassembly.
Figure 4A:
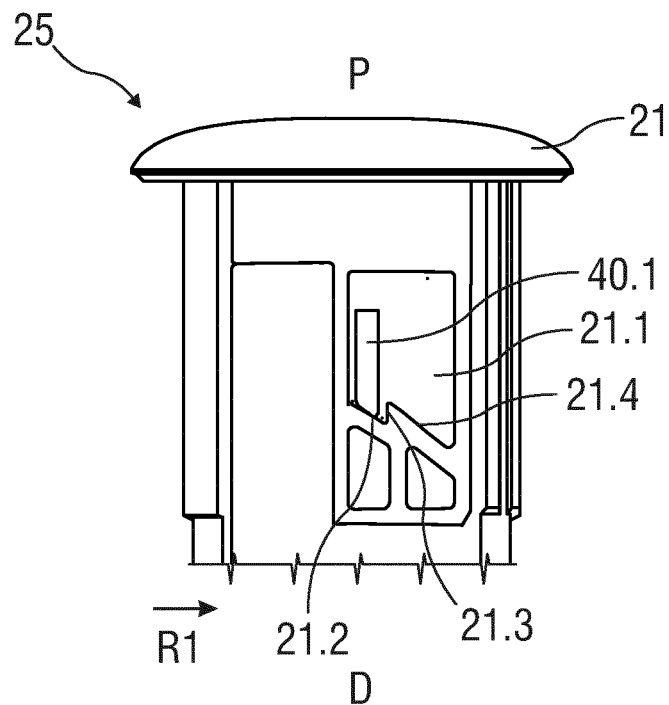
FIG. 4 is a schematic detail view of the drive subassembly showing a plunger release mechanism.
Figure 4B:
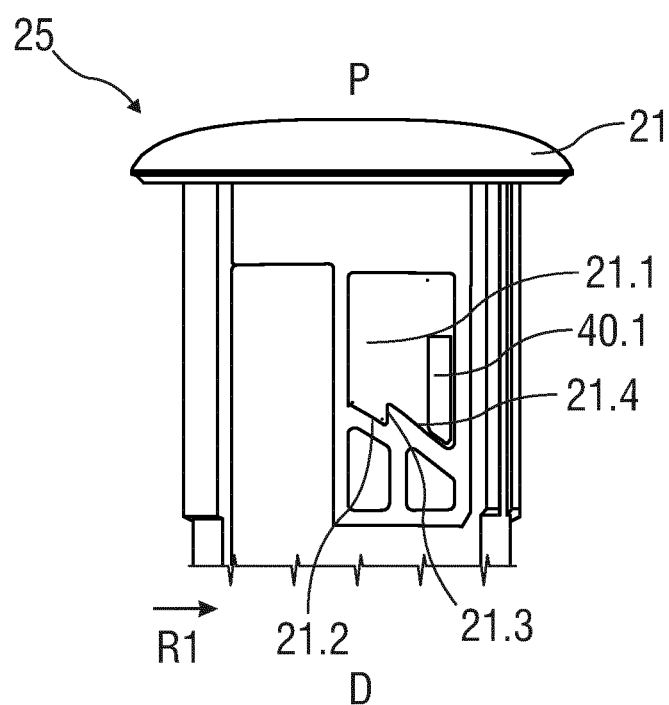

FIG. 3 is a schematic side view of the drive subassembly 10.1. FIGS. 4A and 4B are schematic detail views of the drive subassembly 10.1 showing part of a plunger release mechanism 25.

The plunger release mechanism 25 controls the activation of syringe emptying. The plunger release mechanism 25 is adapted to release the plunger 40 once the sleeve 13 is depressed and reaches a retracted position RP within the housing 11.

The plunger release mechanism 25 comprises a first plunger boss 40.1 arranged on the plunger 40 and a profiled slot 21.1 in the proximal region 21 of the housing 11. The profiled slot 21.1 comprises a first angled surface 21.2 adapted to engage the first plunger boss 40.1 to induce a torque in a first rotational direction R1 to the plunger 40, a wall 21.3 for limiting movement of the first plunger boss 40.1 in the first rotational direction R1 when engaged to the first angled surface 21.2. Furthermore, the profiled slot 21.1 comprises a second angled surface 21.4 adapted to engage the first plunger boss 40.1 to induce a torque in the first rotational direction R1 to the plunger 40.

The first angled surface 21.2 and/or the second angled surface 21.4 may have an angle in a range from 30° to 70° relative to a perpendicular on the longitudinal axis X of the drug delivery device 10 which may also be the longitudinal axis of the plunger 40.

In a first state shown in FIG. 4A, the first plunger boss 40.1 is engaged to the first angled surface 21.2. Due to the drive spring 30 acting on the plunger 40, the first plunger boss 40.1 is pressed against the first angled surface 21.2 in a distal direction D such that a torque is induced to the plunger 40 in the first rotational direction R1 so that the first plunger boss 40.1 slides along the first angled surface 21.2 until it abuts the wall 21.3 so that rotation of the plunger 40 in the first rotational direction R1 is halted.

FIG. 4B shows the plunger release mechanism 25 in a second state. Starting from the first state, the plunger 40 has been moved a distance at least as long as the wall 21.3 in the proximal direction P such that the wall 21.3 no longer limits movement of the first plunger boss 40.1 in the first rotational direction R1. The plunger 40 has then been rotated further in the first rotational direction R1 so that the first plunger boss 40.1 engages the second angled surface 21.4. Due to the drive spring 30 acting on the plunger 40, the first plunger boss 40.1 is pressed against the second angled surface 21.4 in a distal direction D such that a torque is induced to the plunger 40 in the first rotational direction R1 so that the first plunger boss 40.1 slides along the second angled surface 21.4. If the plunger 40 is not otherwise prevented from rotating further, the first plunger boss 40.1 may slide down the second angled surface 21.4 until disengaging it, allowing the plunger 40 to advance in the distal direction D to displace the medicament from the syringe 24.

In an exemplary embodiment, movement of the plunger 40 from the first state in the proximal direction P and onto the second angled surface 21.4 may be achieved by the sleeve 13 interacting with the plunger 40, e.g. by engaging the first plunger boss 40.1 or a further plunger boss or rib on the plunger (not shown).

Figure 5:
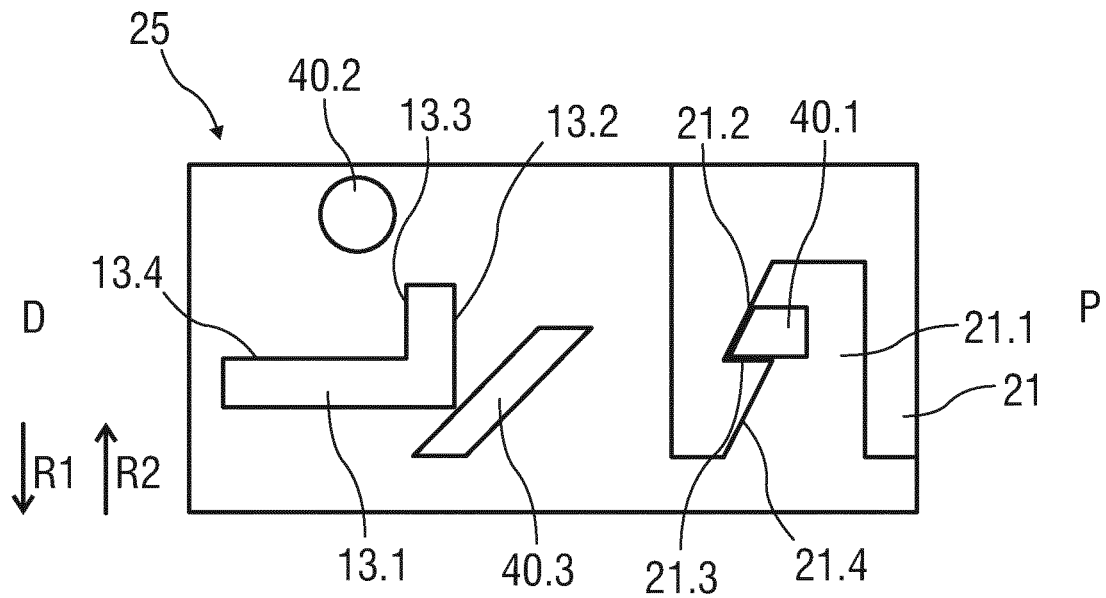
FIG. 5 is a schematic view of an exemplary embodiment of the plunger release mechanism during assembly of the drive subassembly.

FIG. 5 shows the plunger release mechanism during assembly of the drive subassembly 10.1.

The plunger release mechanism 25 is adapted to release the plunger 40 once the sleeve 13 is depressed and reaches a retracted position within the housing 11.

The plunger release mechanism 25 comprises the plunger 40, the proximal region 21, and the sleeve 13 interacting with each other. The sleeve 13 and the proximal region 21 are configured to move only in parallel with the longitudinal axis X relative to each other whereas the plunger 40 can move both in parallel with the longitudinal axis X and rotate about the longitudinal axis X. The parts of the plunger release mechanism 25 may be essentially rigid and require no deformation in order to function correctly.

The parts arranged for engaging the plunger 40, proximal region 21 and sleeve 13 comprise:
  a first plunger boss 40.1 on the plunger 40,
  a second plunger boss 40.2 on the plunger 40,
  an angled plunger rib 40.3 on the plunger 40,
  a profiled slot 21.1 in the proximal region 21 adapted to interact with the first plunger boss 40.1,
  a sleeve rib 13.1 on the sleeve 13 comprising a proximal face 13.2 adapted to interact with the angled plunger rib 40.3, a distal face 13.3 and a longitudinal face 13.4 adapted to interact with the second plunger boss 40.2.

The profiled slot 21.1 comprises a first angled surface 21.2 adapted to engage the first plunger boss 40.1 to induce a torque in a first rotational direction R1 to the plunger 40, a wall 21.3 for limiting movement of the first plunger boss 40.1 in the first rotational direction R1 when engaged to the first angled surface 21.2. Furthermore, the profiled slot 21.1 comprises a second angled surface 21.4 adapted to engage the first plunger boss 40.1 to induce a torque in the first rotational direction R1 to the plunger 40.

During assembly of the drive subassembly 10.1 the plunger 40 with the drive spring 30 is inserted into the proximal region 21. Once the plunger 40 reaches a proximal position the first plunger boss 40.1 is axially aligned with the profiled slot 21.1. By rotating the plunger 40 in a second rotational direction R2 by an angle, e.g. approximately 30°, the first plunger boss 40.1 is moved into the profiled slot 21.1. In this position the first angled surface 21.2 moves the first plunger boss 40.1 against the wall 21.3 by inducing a torque to the plunger 40 in the first rotational direction R1 due to the drive spring 30 biasing the plunger 40 in the distal direction D.

In order to assemble the drug delivery device 10, a syringe 24 may be inserted into the control subassembly which may comprise the distal region 20 of the housing 11.

Afterwards, the drive subassembly 10.1 is inserted into the control subassembly in the distal direction D. The proximal region 21 and the distal region 20 may comprise snap connections to lock them together when assembled. During the final assembly of the drug delivery device 10 the sleeve 13 may be partially depressed to allow initiation of the plunger release mechanism 25, e.g. by an assembly jig (not illustrated) or in a different way.

Figure 6:
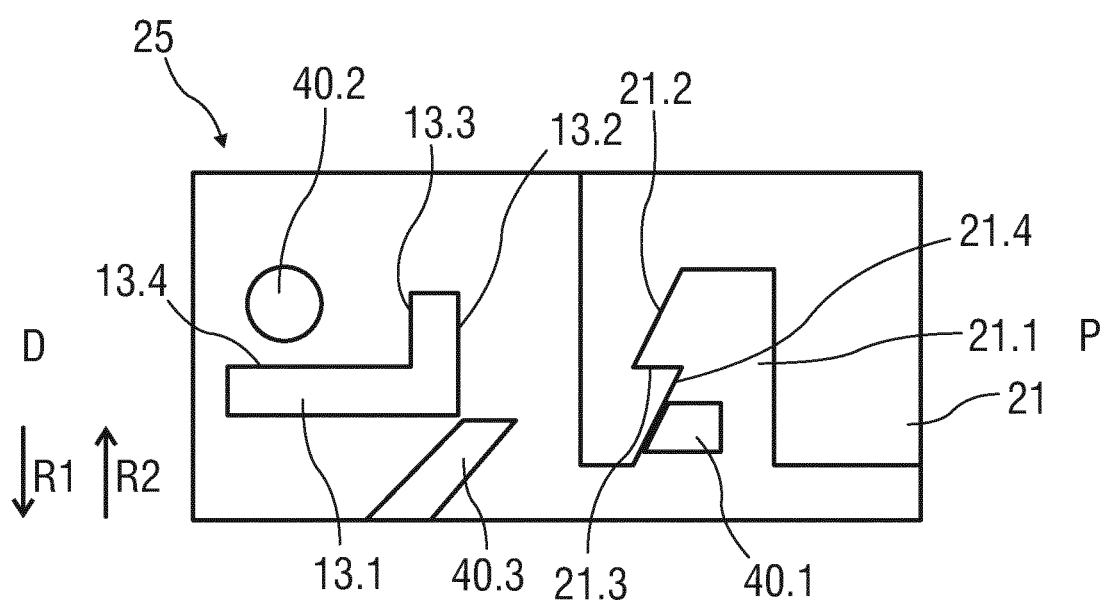
FIG. 6 is a schematic view of the plunger release mechanism during final assembly.
Figure 7:
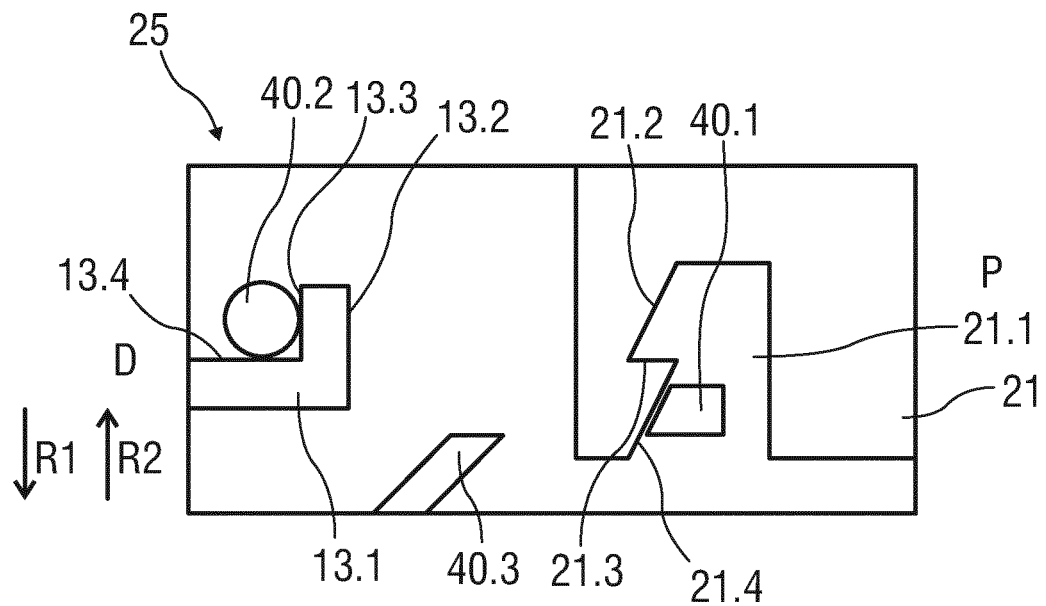
FIG. 7 is a schematic view of the plunger release mechanism after final assembly.

FIG. 6 shows the plunger release mechanism 25 during the final assembly, also referred to as priming. The sleeve rib 13.1 proximally abuts the angled plunger rib 40.3 thereby inducing a torque to the plunger 40 in the first rotational direction R1 and pushing the plunger 40 in the proximal direction P so that the first plunger boss 40.1 moves along the wall 21.3 until it disengages from the wall 21.3. Due to the induced torque, the first plunger boss 40.1 moves in the first rotational direction R1 and engages the second angled surface 21.4. The depression of the sleeve 13 may cease and, due to the first plunger boss 40.1 engaging the second angled surface 21.4 and the drive spring 30 acting on the plunger 40 in the distal direction D, the plunger 40 rotates further in the first rotational direction R1. As the sleeve 13 is not being depressed further it may move in the distal direction D relative to the housing 11, e.g. under the action of a sleeve spring (not illustrated). This movement is limited by the second plunger boss 40.2 abutting the distal face 13.3 on the sleeve rib 13.1. Further rotation of the plunger 40 in the first rotational direction R1 is prevented by the second plunger boss 40.2 abutting the longitudinal face 13.4 of the sleeve rib 13.1. The load of the drive spring 30 is resolved within the proximal region 21 by the first plunger boss 40.1 engaging the profiled slot 21.1. This state of the plunger release mechanism 25 is illustrated in FIG. 7.

A sequence of operation of the drug delivery device 10 may be as follows:

The user removes the cap assembly 12 pulling it in the distal direction D away from the housing 11. Removal of the cap assembly 12 may at the same time remove a protective needle sheath from the needle 17.

The sleeve 13 is in an extended position protruding from the housing 11 in the distal direction D. The extended position may be defined by the second plunger boss 40.2 proximally abutting the distal face 13.3 of the sleeve rib 13.

The user may then press the drug delivery device 10 with the sleeve 13 ahead against an injection site, e.g. a patient's skin thereby moving the sleeve 13 from the extended position towards a retracted position against the bias of the shroud spring.

Figure 8:
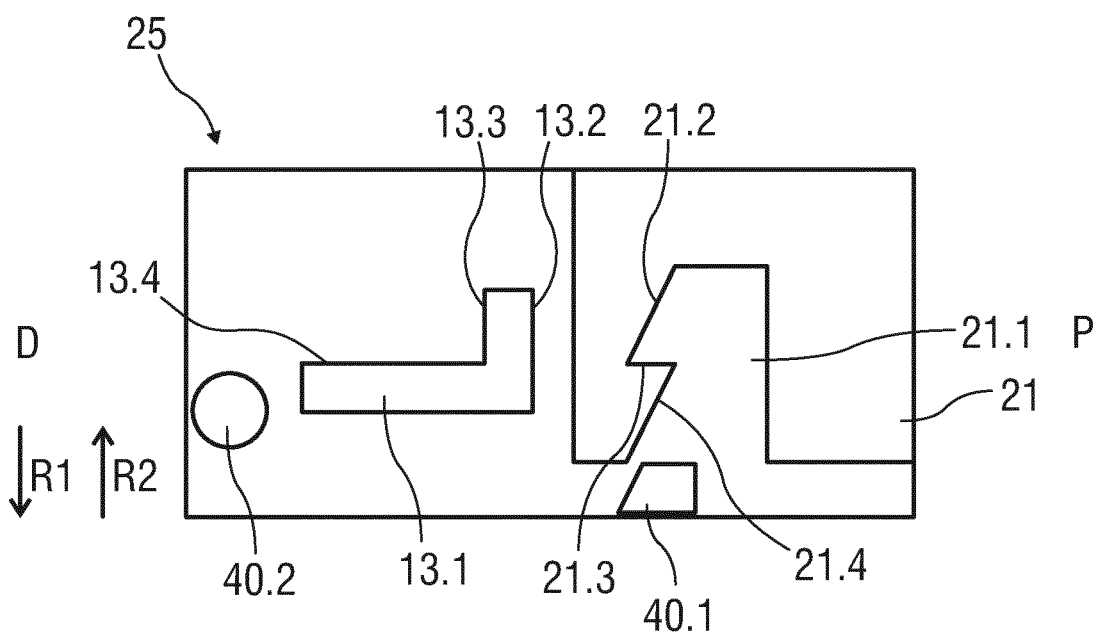
FIG. 8 is a schematic view of the plunger release mechanism after depression of a sleeve.

FIG. 8 is a schematic view of the plunger release mechanism 25 after depression of the sleeve 13 into the retracted position. As the sleeve 13 is being moved from the extended position towards the retracted position the second plunger boss 40.2 moves (starting from the position shown in FIG. 7) relative to the sleeve 13 in the distal direction D guided along the longitudinal face 13.4 of the sleeve rib 13.1.

In an exemplary embodiment the longitudinal face 13.4 of the sleeve rib 13.1 may comprise an interruption or bump feature (not illustrated) for creating an increase in the force required to depress the sleeve 13 further. This may be used to indicate to the user that needle insertion would commence with further depression of the sleeve 13. Up until this point, the user is free to remove the drug delivery device 10 from the injection site and reposition as the sleeve 13 will re-extend to its initial position under the force of the shroud spring.

If the user continues pressing the drug delivery device 10 against the injection site the sleeve 13 is moved into the retracted position exposing the needle 17 and inserting it into the injection site.

Once the sleeve 13 is depressed into the retracted position, and the needle 17 inserted, the second plunger boss 40.2 has moved distally beyond the sleeve rib 13 such that the plunger 40 is no longer prevented from rotating in the first rotational direction R1 due to the torque induced by the drive spring 30 and the first plunger boss 40.1 engaging the second angled surface 21.4 on the profiled slot 21.1. The plunger 40 rotates in the first rotational direction R1 due to this torque and the first plunger boss 40.1 comes clear of the profiled slot 21.1.

The plunger 40 is thus released and advances the piston 23 in the distal direction D displacing the medicament from the syringe 24 through the needle 17. The release of the first or second plunger boss 40.1, 40.2 may provide audible feedback that delivery of the medicament has started.

Figure 9:
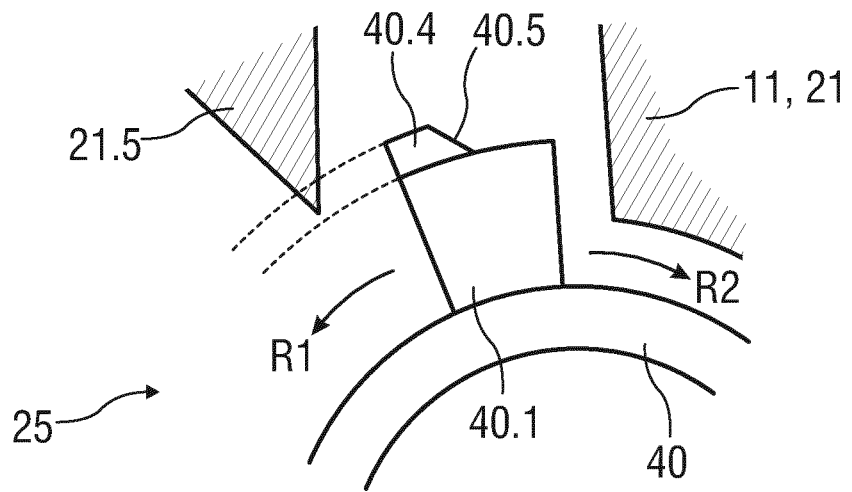
FIG. 9 is a schematic detail view of an exemplary embodiment of the drive subassembly.

FIG. 9 is a schematic detail view of an exemplary embodiment of the drive subassembly 10.1. The housing 11, in particular the proximal region 21 thereof, comprises a plastically and/or resiliently deformable housing protrusion 21.5 protruding radially inwards, i.e. towards the plunger 40. A plunger boss, in particular the first plunger boss 40.1 is adapted to abut the housing protrusion 21.5 when the plunger 40 rotates in the first rotational direction R1 during priming such that the housing protrusion 21.5 is deformed upon further rotation of the plunger 40 thereby restraining said rotation. The plunger boss, in particular the first plunger boss 40.1, may comprise a radial plunger protrusion 40.4 adapted to abut the housing protrusion 21.5 upon rotation of the plunger 40. In an exemplary embodiment, the plunger protrusion 40.4 may be plastically and/or resiliently deformable instead of or in addition to the plastical and/or resilient deformability of the housing protrusion 21.5. The plunger protrusion 40.4 may comprise a chamfer 40.5 towards a second rotational direction R2 opposing the first rotational direction R1, wherein the chamfer 40.5 is adapted to engage the housing protrusion 21.5 when the plunger 40 is rotated in the second rotational direction R2 during assembly of the plunger 40 into the housing 11, in particular into the proximal region 21 thereof. In an exemplary embodiment, the plunger protrusion 40.2 does not have a chamfer on its face towards the first rotational direction R1. Thus, a torque on the plunger 40 required for assembling the plunger 40 into the housing 11 is less than a torque required to rotate the plunger 40 during priming and the housing protrusion 21.5 is deformed to a lesser extent during assembly than during priming. If the drive subassembly 10.1 is dropped and hits the ground, in particular with the distal end ahead, the housing protrusion 21.5 prevents inadvertent release of the plunger 40.

Figure 10:
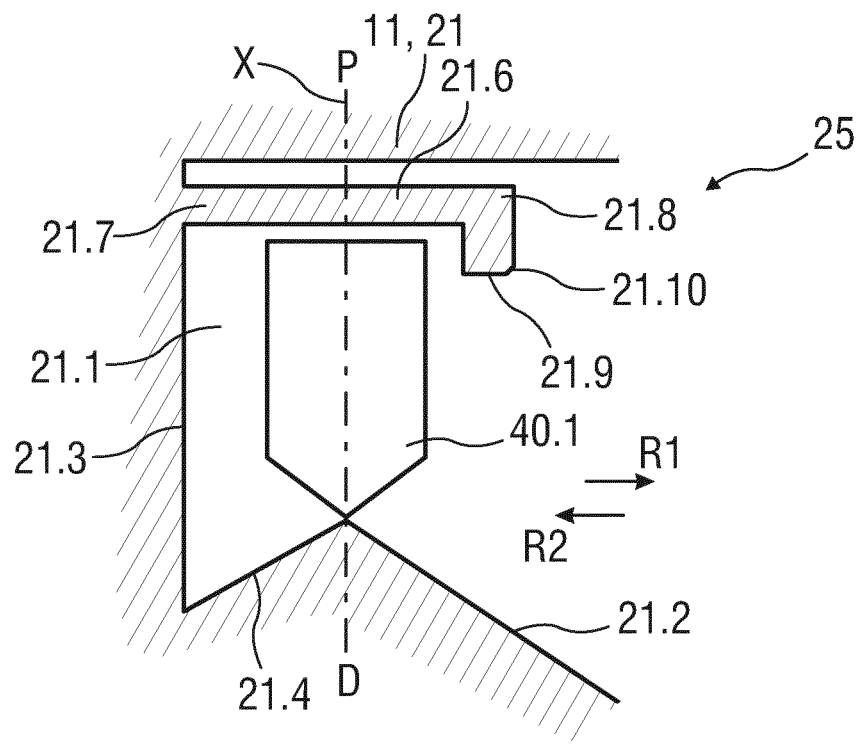
FIG. 10 is a schematic detail view of an exemplary embodiment of the drive subassembly.

FIG. 10 is a schematic detail view of an exemplary embodiment of the drive subassembly 10.1. In this embodiment, the profiled slot 21.1 comprises a first angled surface 21.2 adapted to engage the first plunger boss 40.1 to induce a torque in a first rotational direction R1 to the plunger 40 and a second angled surface 21.4 adapted to engage the first plunger boss 40.1 to induce a torque in a second rotational direction R2 opposing the first rotational direction R1 to the plunger 40. A wall 21.3 is provided for limiting movement of the first plunger boss 40.1 in the second rotational direction R2 when engaged to the second angled surface 21.4.

During assembly of the drive subassembly 10.1 the plunger 40 with the drive spring 30 is inserted into the proximal region 21. Once the plunger 40 reaches a proximal position the first plunger boss 40.1 is axially aligned with the profiled slot 21.1. By rotating the plunger 40 in the second rotational direction R2, the first plunger boss 40.1 is moved into the profiled slot 21.1. In this position the second angled surface 21.4 moves the first plunger boss 40.1 against the wall 21.3 by inducing a torque to the plunger 40 in the second rotational direction R2 due to the drive spring 30 biasing the plunger 40 in the distal direction D.

A resilient, transversal housing beam 21.6 is provided within the profiled slot 21.1 near the proximal end thereof, the housing beam 21.6 essentially extending in a transversal direction relative to the longitudinal axis X. The housing beam 21.6 comprises a fixed end 21.7 coupled to the housing 11, e.g. the proximal region 21 thereof, in particular the wall 21.3, and a free end 21.8. The housing beam 21.6 is axially positioned to restrain movement of the first plunger boss 40.1 in the proximal direction P if the drive subassembly 10.1 is dropped and hits the ground, in particular with the distal end ahead. Restraining this movement reduces the risk that the plunger 40 could be rotated by any torsion stored in the drive spring 30 thus inadvertently releasing the plunger 40.

In an exemplary embodiment, the free end 21.8 of the housing beam 21.6 comprises a distal protrusion 21.9. A chamfer 21.10 is provided on the distal protrusion 21.9 adapted to abut the plunger boss 40.1 when the plunger 40 is rotated in the second rotational direction R2 during assembly of the plunger 40 into the housing 11 such that the housing beam 21.6 is deflected in the proximal direction P upon further rotation of the plunger 40 in the second rotational direction R2 to allow the plunger boss 40.1 to enter the profiled slot 21.1. During priming, the plunger 40 is rotated in the first rotational direction R1 until abutting the distal protrusion 21.9. Further rotation of the plunger 40 caused by the angled plunger rib 40.3 engaging the sleeve rib 13.1 deflects the housing beam 21.6 so the first plunger boss 40.1 can move further in the first rotational direction R1.

Figure 11:
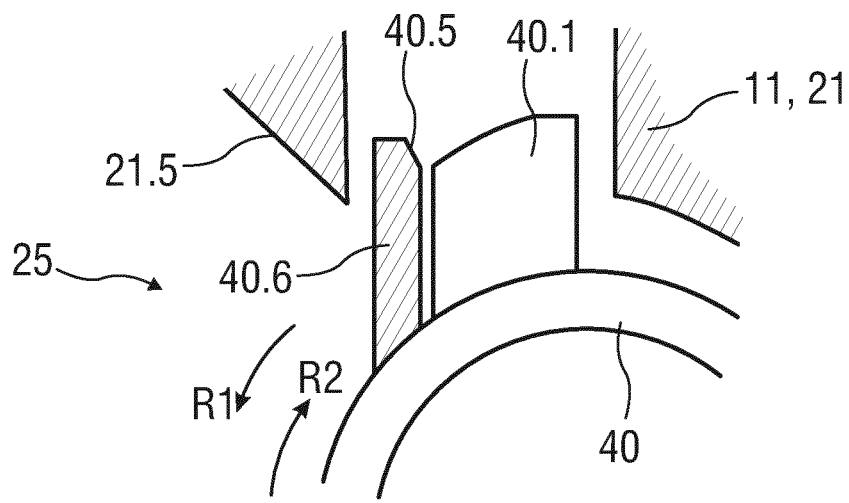
FIG. 11 is a schematic detail view of an exemplary embodiment of the drive subassembly.

FIG. 11 is a schematic detail view of an exemplary embodiment of the drive subassembly 10.1. The housing 11, in particular the proximal region 21 thereof, comprises a plastically and/or resiliently deformable housing protrusion 21.5 protruding radially inwards, i.e. towards the plunger 40. A plunger boss, in particular a resilient additional plunger boss 40.6 is adapted to abut the housing protrusion 21.5 when the plunger 40 rotates in the first rotational direction R1 such that the housing protrusion 21.5 is deformed upon further rotation of the plunger 40 thereby restraining said rotation. In an exemplary embodiment, the additional plunger boss 40.6 may be plastically and/or resiliently deformable instead of or in addition to the plastical and/or resilient deformability of the housing protrusion 21.5. The additional plunger boss 40.6 may comprise a chamfer 40.5 towards a second rotational direction R2 opposing the first rotational direction R1, wherein the chamfer 40.3 is adapted to engage the housing protrusion 21.5 when the plunger is rotated in the second rotational direction R2 during assembly of the plunger 40 into the housing 11, in particular the proximal region 21 thereof. In an exemplary embodiment, the additional plunger boss 40.6 does not have a chamfer on its face towards the first rotational direction R1. Thus, a torque on the plunger 40 required for assembling the plunger 40 into the housing 11 is less than a torque required to rotate the plunger 40 during priming and the housing protrusion 21.5 is deformed to a lesser extent during assembly than during priming. If the drive subassembly 10.1 is dropped and hits the ground, in particular with the distal end ahead, the housing protrusion 21.5 prevents inadvertent release of the plunger 40.

Figure 12:
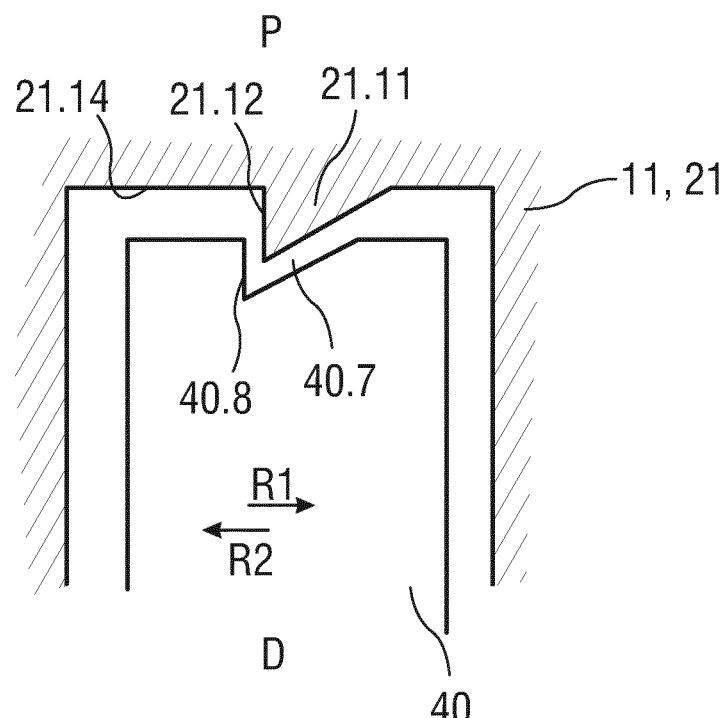
FIG. 12 is a schematic detail view of an exemplary embodiment of the drive subassembly.

FIG. 12 is a schematic detail view of an exemplary embodiment of a proximal end of the plunger 40. A ramped housing protrusion 21.11 protrudes from a proximal wall 21.14 of the housing 11, in particular the proximal region 21 thereof, in the distal direction D. A proximal face of the plunger 40 comprises a recess 40.7 corresponding to the housing protrusion 21.11 such that the housing protrusion 21.11 restrains rotation of the plunger 40 in the first rotational direction R1. The housing protrusion 21.11 is adapted to abut the plunger boss 40.1 when the plunger 40 is rotated in the second rotational direction R2 during assembly of the plunger 40 into the housing 11 such that the housing protrusion 21.11 is resiliently deformed upon further rotation of the plunger 40 in the second rotational direction R2 to allow the housing protrusion 21.11 to snap into the recess 40.7. During priming, the plunger 40 is rotated in the first rotational direction R1 until an edge 21.12 on the housing protrusion 21.11 abuts an edge 40.8 on the recess 40.7. Further rotation of the plunger 40 in the first rotational direction R1 caused by the angled plunger rib 40.3 engaging the sleeve rib 13.1 deforms the housing protrusion 21.11.

Figure 13:
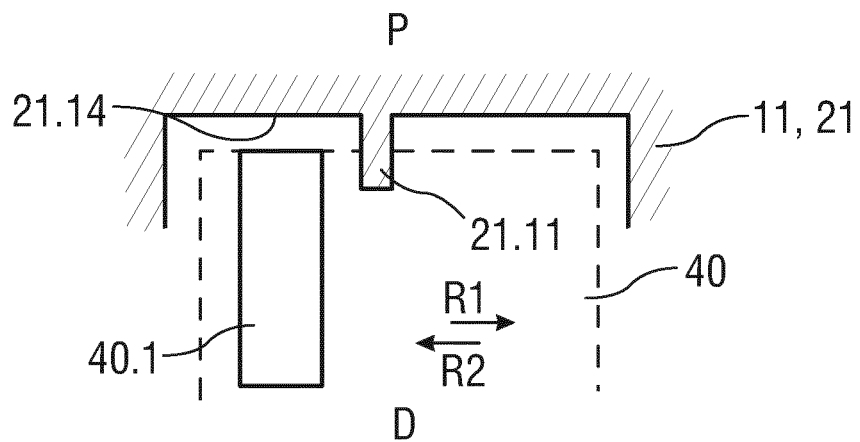
FIG. 13 is a schematic detail view of an exemplary embodiment of the drive subassembly.

FIG. 13 is a schematic detail view of an exemplary embodiment of the drive subassembly 10.1. A distal housing protrusion 21.11 protrudes from a proximal wall 21.14 of the housing 11, in particular the proximal region 21 thereof, in the distal direction D so as to abut the first plunger boss 40.1 upon rotation of the plunger 40 thereby restraining rotation thereof. The housing protrusion 21.11 is adapted to abut the plunger boss 40.1 when the plunger 40 is rotated in the second rotational direction R2 during assembly of the plunger 40 into the housing 11 such that the housing protrusion 21.11 is resiliently deformed upon further rotation of the plunger 40 in the second rotational direction R2 to allow the first plunger boss 40.1 to pass. During priming, the plunger 40 is rotated in the first rotational direction R1 until the first plunger boss 40.1 abuts the housing protrusion 21.11. Further rotation of the plunger 40 in the first rotational direction R1 caused by the angled plunger rib 40.3 engaging the sleeve rib 13.1 deforms the housing protrusion 21.11 allowing the first plunger boss 40.1 to pass.

Figure 14:
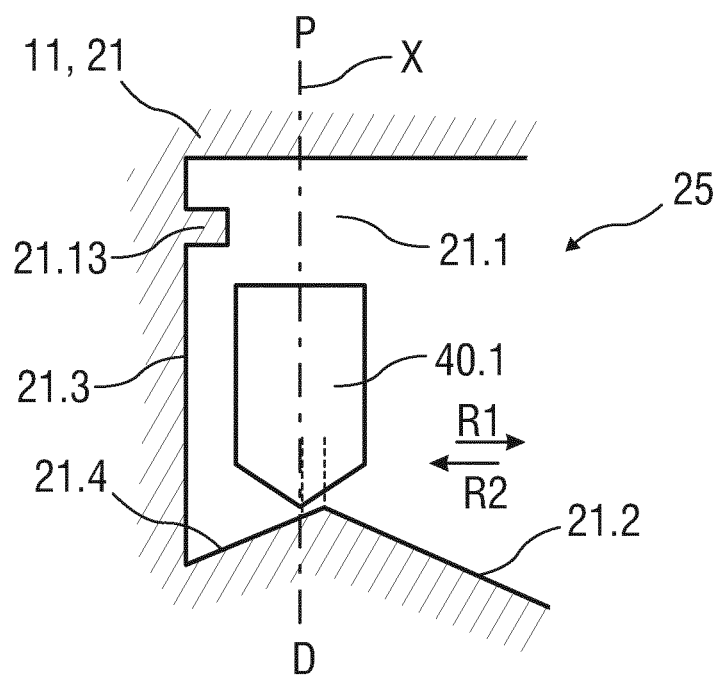
FIG. 14 is a schematic detail view of an exemplary embodiment of the drive subassembly.

FIG. 14 is a schematic detail view of an exemplary embodiment of the drive subassembly 10.1. In this embodiment, the profiled slot 21.1 comprises a first angled surface 21.2 adapted to engage the first plunger boss 40.1 to induce a torque in a first rotational direction R1 to the plunger 40 and a second angled surface 21.4 adapted to engage the first plunger boss 40.1 to induce a torque in a second rotational direction R2 opposing the first rotational direction R1 to the plunger 40. A wall 21.3 is provided for limiting movement of the first plunger boss 40.1 in the second rotational direction R2 when engaged to the second angled surface 21.4.

During assembly of the drive subassembly 10.1 the plunger 40 with the drive spring 30 is inserted into the proximal region 21. Once the plunger 40 reaches a proximal position the first plunger boss 40.1 is axially aligned with the profiled slot 21.1. By rotating the plunger 40 in the second rotational direction R2, the first plunger boss 40.1 is moved into the profiled slot 21.1. In this position the second angled surface 21.4 moves the first plunger boss 40.1 against the wall 21.3 by inducing a torque to the plunger 40 in the second rotational direction R2 due to the drive spring 30 biasing the plunger 40 in the distal direction D.

A transversal protrusion 21.13 is provided within the profiled slot 21.1 near the proximal end thereof, the transversal protrusion 21.13 essentially extending in a transversal direction relative to the longitudinal axis X. The transversal protrusion 21.13 is fixed to the housing 11, e.g. the proximal region 21 thereof, in particular the wall 21.3. The transversal protrusion 21.13 is axially positioned to restrain movement of the first plunger boss 40.1 in the proximal direction P if the drive subassembly 10.1 is dropped and hits the ground, in particular with the distal end ahead. Restraining this movement reduces the risk that the plunger 40 could be rotated by any torsion stored in the drive spring 30 thus inadvertently releasing the plunger 40.

Figure 15:
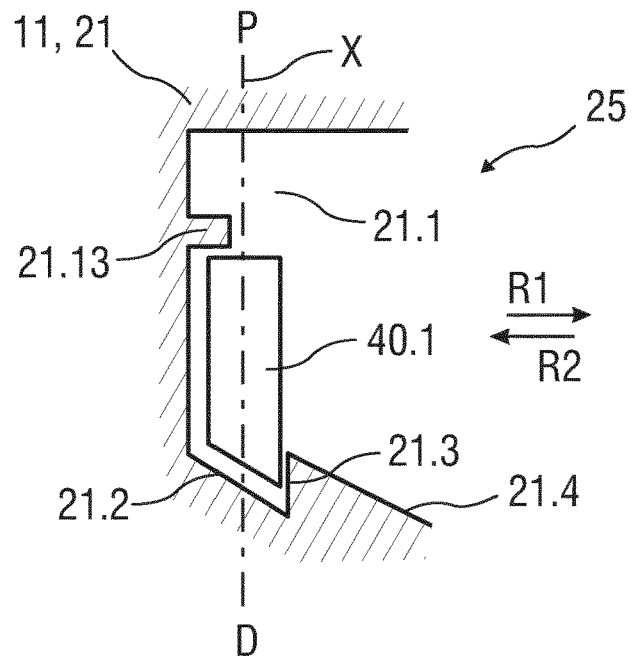
FIG. 15 is a schematic detail view of an exemplary embodiment of the drive subassembly.

FIG. 15 is a schematic detail view of an exemplary embodiment of the drive subassembly 10.1. In this embodiment, the profiled slot 21.1 is configured essentially as in FIGS. 5 to 8.

A transversal protrusion 21.13 is provided within the profiled slot 21.1 near the proximal end thereof, the transversal protrusion 21.13 essentially extending in a transversal direction relative to the longitudinal axis X. The transversal protrusion 21.13 is fixed to the housing 11, e.g. the proximal region 21 thereof. The transversal protrusion 21.13 is axially positioned to restrain movement of the first plunger boss 40.1 in the proximal direction P if the drive subassembly 10.1 is dropped and hits the ground, in particular with the distal end ahead.

Restraining this movement reduces the risk that the plunger 40 could be rotated by any torsion stored in the drive spring 30 thus inadvertently releasing the plunger 40.

In an exemplary embodiment, the transversal protrusion 21.13 may exhibit rounded or chamfered edges. The transversal protrusion 21.13 may be axially positioned to allow a small clearance, e.g. 0.5 mm, between the first plunger boss 40.1 and the transversal protrusion 21.13 during priming when the first plunger boss 40.1 disengages the wall 21.3 and engages the second angled surface 21.4.

Figure 16:
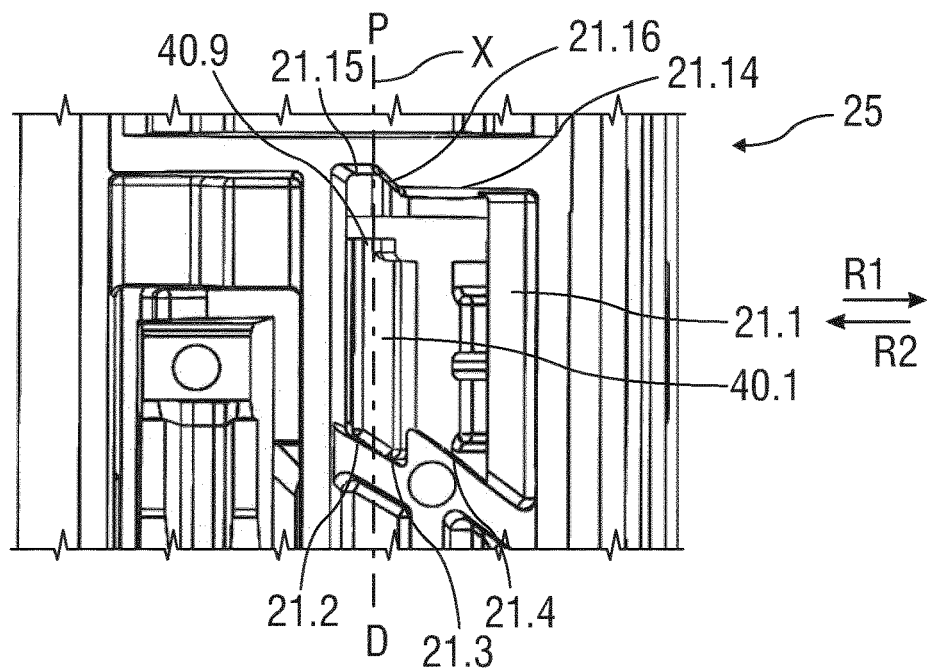
FIG. 16 is a schematic detail view of an exemplary embodiment of the drive subassembly.

FIG. 16 is a schematic detail view of an exemplary embodiment of the drive subassembly 10.1. In this embodiment, the profiled slot 21.1 is configured essentially as in FIGS. 5 to 8. The first plunger boss 40.1 comprises a proximal boss 40.9 protruding in the proximal direction P. A proximal wall 21.14 of the profiled slot 21.1 comprises an indent 21.15 adapted to receive the proximal boss 40.9 so as to restrain rotation of the plunger 40 in the first rotational direction R1 when the proximal boss 40.9 is received within the indent 21.15. A ramp 21.16 on the indent 21.15 is adapted to guide the proximal boss 40.9 into the indent 21.15 and rotate the plunger 40 in the second rotational direction R2, if required, so that the first plunger boss 40.1 remains aligned with the first angled surface 21.2. An axial clearance between the proximal boss 40.9 and the proximal wall 21.14 during priming is such that the first plunger boss 40.1 can disengage the wall 21.3 and engage the second angled surface 21.4.

Figure 17:
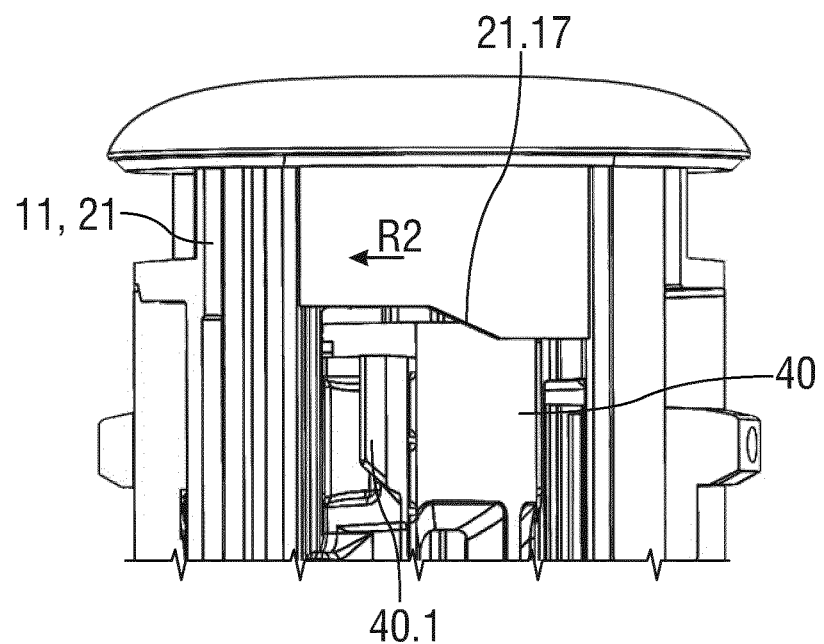
FIG. 17 is a schematic detail view of an exemplary embodiment of the drive subassembly.

FIG. 17 is a schematic detail view of the drive subassembly 10.1, in particular the proximal region 21 of the housing 11 and the proximal end of the plunger 40. A ramp 21.17 is provided on the proximal region 21 adapted to engage a boss, e.g. the first plunger boss 40.1, the second plunger boss 40.2 or yet another boss, on the plunger 40 during assembly of the plunger 40 into the housing 11 and to rotate the plunger 40 in the second rotational direction R2 upon movement of the plunger 40 in the proximal direction P relative to the housing 11 until the plunger 40 reaches a proximal end position from which it may subsequently rotated such that the first plunger boss 40.1 is moved into the profiled slot 21.1.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-06-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 10 drug delivery device
10.1 drive subassembly
11 housing
11a window
12 cap assembly
13 sleeve
13.1 sleeve rib
13.2 proximal face
13.3 distal face
13.4 longitudinal face
17 needle
20 distal region
21 proximal region
21.1 profiled slot
21.2 first angled surface
21.3 wall
21.4 second angled surface
21.5 housing protrusion
21.6 housing beam
21.7 fixed end
21.8 free end
21.9 distal protrusion
21.10 chamfer
21.11 housing protrusion
21.12 edge
21.13 transversal protrusion
21.14 proximal wall
21.15 indent
21.16 ramp
21.17 ramp
22 button
23 piston
24 syringe
25 plunger release mechanism
25.1 housing protrusion
30 drive spring
40 plunger
40.1 first plunger boss
40.2 second plunger boss
40.3 angled plunger rib
40.4 plunger protrusion
40.5 chamfer
40.6 additional plunger boss
40.7 recess
40.8 edge
40.9 proximal boss
D distal end, distal direction
P proximal end, proximal direction
R1 first rotational direction
X longitudinal axis

The invention claimed is:

1. A drug delivery device comprising:
a drive subassembly comprising a housing and a plunger, wherein the plunger is adapted to be rotated between a locked position, in which the plunger is prevented from advancing, and a released position, in which the plunger is advanceable,
at least one restraining component adapted to restrain rotation of the plunger from the locked position towards the released position, and
a control subassembly comprising a distal region of the housing adapted to receive a syringe and a sleeve coupled to the housing to permit movement of the sleeve relative to the housing to release the plunger;
wherein the at least one restraining component comprises a plunger boss on the plunger and an indent in the housing, the plunger boss having a proximal boss protruding in a proximal direction adapted to be received within the indent to restrain rotation of the plunger from the locked position towards the released position.

2. The drug delivery device of claim 1, further comprising the syringe containing a medicament.

3. The drug delivery device of claim 1, wherein the at least one restraining component is configured to restrain rotation of the plunger from the locked position towards the released position during a priming step.

4. The drug delivery device of claim 1, wherein the at least one restraining component comprises a deformable housing protrusion on the housing and a plunger boss or edge on the plunger adapted to:
abut the housing protrusion when the plunger is rotated from the locked position towards the released position, and
deform the housing protrusion upon further rotation of the plunger towards the released position.

5. The drug delivery device of claim 4, wherein the housing protrusion is configured to protrude radially inwards or in a distal direction.

6. The drug delivery device of claim 4, wherein the plunger boss is resiliently or plastically deformable.

7. The drug delivery device of claim 4, wherein the plunger boss comprises a radial plunger protrusion adapted to abut the housing protrusion.

8. The drug delivery device of claim 4, wherein a plunger protrusion or the plunger boss comprises a chamfer adapted to engage the housing protrusion when the plunger is rotated from the released position towards the locked position.

9. The drug delivery device of claim 4, wherein the edge is arranged on a recess within a proximal face of the plunger.

10. The drug delivery device of claim 1, wherein the at least one restraining component comprises a transversal component and a plunger boss on the plunger adapted to abut the transversal component when in the locked position and being moved in a proximal direction to restrain proximal movement of the plunger.

11. The drug delivery device of claim 10, wherein the transversal component is a housing beam comprising a fixed end coupled to the housing and a free end, the free end comprising a distal protrusion adapted to abut the plunger boss upon rotation of the plunger from the locked position towards the released position.

12. The drug delivery device of claim 11, wherein the housing beam is resiliently or plastically deformable.

13. The drug delivery device of claim 11, wherein the distal protrusion comprises a chamfer adapted to engage the plunger boss when the plunger is rotated from the released position towards the locked position.

14. The drug delivery device of claim 10, wherein the transversal component comprises at least one rounded or chamfered edge to engage the plunger boss.

15. The drug delivery device of claim 10, wherein the transversal component is axially positioned to allow an axial clearance between the plunger boss and the transversal component when the plunger is being moved out of the locked position.

16. The drug delivery device of claim 1, wherein the indent comprises a ramp adapted to guide a proximal boss of the plunger boss into the indent and rotate the plunger towards the locked position.

17. The drug delivery device of claim 1, wherein a ramp is provided on the housing adapted to engage the plunger during assembly of the plunger into the housing and to rotate the plunger towards the locked position upon movement of the plunger in a proximal direction relative to the housing.

18. The drug delivery device of claim 1, further comprising a drive spring adapted to bias the plunger in a distal direction relative to the housing.

19. The drug delivery device of claim 1, wherein the sleeve comprises a sleeve rib having a longitudinal face interacting with a plunger boss, wherein, as the sleeve is being moved from an extended position towards a retracted position, the plunger boss moves relative to the sleeve in a distal direction guided along the longitudinal face of the sleeve rib until the plunger boss has moved distally beyond the sleeve rib such that the plunger is no longer prevented from rotating in a first rotational direction.

20. A drug delivery device comprising:
a drive subassembly comprising a housing and a plunger, wherein the plunger is adapted to be rotated between a locked position, in which the plunger is prevented from advancing, and a released position, in which the plunger is advanceable,
at least one restraining component adapted to restrain rotation of the plunger from the locked position towards the released position, and a control subassembly comprising a distal region of the housing adapted to receive a syringe and a sleeve coupled to the housing to permit movement of the sleeve relative to the housing to release the plunger,
wherein the at least one restraining component comprises a plunger boss on the plunger and an indent in the housing,
wherein the indent is formed at a proximal end of a profiled slot in the housing, and
wherein the plunger boss has a proximal boss adapted to be received within the indent.

21. The drug delivery device of claim 1, wherein the proximal boss protrudes from the plunger boss.

* * * * *